United States Patent

Misener et al.

(10) Patent No.: US 8,760,645 B2
(45) Date of Patent: Jun. 24, 2014

(54) METHOD OF NORMALIZING A FLUORESCENCE ANALYZER

(75) Inventors: Garland Christian Misener, Portland, ME (US); James Edward Milan, Buxton, ME (US); Robert W. Lachapelle, Leeds, ME (US)

(73) Assignee: IDEXX Laboratories Inc., Westbrook, MA (US)

( * ) Notice: Subject to any disclaimer, the term of this patent is extended or adjusted under 35 U.S.C. 154(b) by 332 days.

(21) Appl. No.: 13/114,261

(22) Filed: May 24, 2011

(65) Prior Publication Data

US 2012/0300205 A1  Nov. 29, 2012

(51) Int. Cl.
- *G01J 3/00* (2006.01)
- *G01J 3/30* (2006.01)
- *G01N 21/25* (2006.01)

(52) U.S. Cl.
USPC ............................ 356/300; 356/318; 356/417

(58) Field of Classification Search
USPC ............ 356/300–334, 417; 422/82.07–82.08; 250/458.1–461.2; 436/172; 600/317
See application file for complete search history.

(56) References Cited

U.S. PATENT DOCUMENTS

| | | | |
|---|---|---|---|
| 3,967,113 A | 6/1976 | Soodak et al. | |
| 4,299,486 A | 11/1981 | Nogami et al. | |
| 4,531,834 A | 7/1985 | Nogami | |
| 4,577,338 A | 3/1986 | Takahashi et al. | |
| 4,779,982 A | 10/1988 | Koshi et al. | |
| 4,798,463 A | 1/1989 | Koshi | |
| 4,804,845 A | 2/1989 | Takeuchi | |
| 4,857,451 A | 8/1989 | Schwartz | |
| 4,877,583 A | 10/1989 | Miwa et al. | |
| 4,921,350 A * | 5/1990 | Giebeler | 356/320 |
| 4,945,245 A | 7/1990 | Levin | |
| 5,084,394 A | 1/1992 | Vogt et al. | |
| 5,093,234 A | 3/1992 | Schwartz | |
| 5,166,052 A | 11/1992 | Cercek et al. | |
| 5,173,434 A | 12/1992 | Morris et al. | |
| 5,270,788 A | 12/1993 | Cercek et al. | |
| 5,591,981 A | 1/1997 | Heffelfinger et al. | |
| 5,672,515 A | 9/1997 | Furlong | |
| 5,675,517 A | 10/1997 | Stokdijk | |
| 5,697,373 A | 12/1997 | Richards-Kortum et al. | |
| 5,833,617 A | 11/1998 | Hayashi | |

(Continued)

OTHER PUBLICATIONS

Technical Note: An introduction to Fluorescence Measurements. Turner Designs. 1995 [date retrieved Aug. 2, 2012]. Retrieved from the Internet: <URL: http://www.turnerdesigns.com/t2/doc/appnotes/998-0050.pdf> entire document.

(Continued)

*Primary Examiner* — Gregory J Toatley, Jr.
*Assistant Examiner* — Hina F Ayub
(74) *Attorney, Agent, or Firm* — Carter, DeLuca, Farrell & Schmidt, LLP

(57) ABSTRACT

A method of normalizing an analyzer response value of a fluorescence analyzer is provided. The method includes measuring an excitation spectrum of the analyzer and measuring an emission sensitivity spectrum of the analyzer. Next, a normalization factor based at least in part upon the excitation spectrum of the analyzer and the emission sensitivity spectrum of the analyzer is determined. The sample is then analyzed to obtain an uncorrected analyzer response value. A normalized analyzer response value is calculated based at least in part upon the uncorrected analyzer response value and the normalization factor.

16 Claims, 10 Drawing Sheets

(56) References Cited

U.S. PATENT DOCUMENTS

| | | |
|---|---|---|
| 5,850,623 A | 12/1998 | Carman, Jr. et al. |
| 6,070,096 A | 5/2000 | Hayashi |
| 6,429,936 B1 | 8/2002 | Scaduto |
| 6,535,278 B1 | 3/2003 | Imura |
| 6,661,909 B2 | 12/2003 | Youvan et al. |
| 6,686,206 B2 | 2/2004 | Levitsky et al. |
| 6,985,224 B2 | 1/2006 | Hart |
| 7,359,815 B2 | 4/2008 | Pirzer et al. |
| 7,502,099 B2 | 3/2009 | Imura |
| 7,583,369 B2 | 9/2009 | Gunji |
| 7,616,317 B2 | 11/2009 | Misener et al. |
| 7,713,741 B2 | 5/2010 | Resch-Genger et al. |
| 2010/0219333 A1* | 9/2010 | Resch-Genger et al. .. 250/252.1 |
| 2010/0254854 A1 | 10/2010 | Rich et al. |

OTHER PUBLICATIONS

PCT International Search Report mailed Aug. 17, 2012 in corresponding International Application No. PCT/US2012/039066.

* cited by examiner

METHOD OF NORMALIZING A FLUORESCENCE ANALYZER

BACKGROUND

1. Technical Field

The present disclosure relates to fluorescence analysis and, more particularly, to methods of normalizing fluorescence analyzers according to specific wavelength characteristics thereof.

2. Background of Related Art

Filter fluorometry refers generally to the process of illuminating a sample and quantitating the resulting, detected fluorescence signal. A filter fluorometer, designed to perform fluorometry, employs one or more light sources, optical filters, and detectors to select the wavelength ranges of both the illuminating light and the light detected. Generally, these two kinds of wavelength ranges do not overlap to any appreciable extent, and the detection wavelengths are longer than the illumination wavelengths. Using a predetermined calibration curve, the detected signal is correlated to the amount of fluorescent component present in the sample. For example, filter fluorometry (hereafter, simply "fluorometry") may be used to measure the concentration of certain electrolytes in blood plasma or serum by their effect on the fluorescence of a test device, e.g., a slide.

Currently, electrolyte detection via fluorometry involves the use of sensors which include reagents, e.g., electrolyte-specific fluoroionophores (for $Na^+$ and $K^+$ detection) or acridinium reagents (for $Cl^-$ detection). Initially, a slide containing only the appropriate sensor (e.g., the "dry" slide) is read by an analyzer designed to perform fluorometry on such slides, in order to measure an "early" fluorescence intensity. This "early" fluorescence may be an average "early" fluorescence intensity of multiple "early" fluorescence intensity measurements. Next, the sample to be tested is added to and allowed to interact with the slide. The slide, including the sample (e.g., the "wet" slide), is again read by the analyzer in order to measure a "late" fluorescence intensity. Similarly as above, this "late" fluorescence intensity may be an average of multiple "late" fluorescence intensity measurements. These measured values are then corrected in accordance with a fluorescence baseline and an analyzer response is calculated based on the ratio of the baseline-corrected "early" and "late" fluorescence intensity measurements. More specifically, the analyzer response is calculated according to:

$$AR_e = \frac{I_{late,e} - I_{baseline,e}}{I_{early,e} - I_{baseline,e}} \qquad \text{EQ 1}$$

Where "AR" is the analyzer response for the given electrolyte, "e," and wherein the "I" values are the measured fluorescence intensities (or averages thereof). Note that "early" fluorescence intensity measurement may also be obtained soon after sample addition.

The analyzer response "AR," may then be used, in accordance with the slide's lot calibration, to determine the specific electrolyte's concentration in the sample under test. However, there are multiple sources of variability, e.g., analyzer-to-analyzer variability (wavelength variation in the fluorescence detection module, dispensed volume variation, incubation temperature variation, timing variation, etc.) and also sensor-to-sensor variability, that may produce different analyzer responses for the same sample. It is therefore necessary to correct, or "normalize" these analyzer responses in order to accurately determine the electrolyte concentration in a given sample.

Current methods of normalizing analyzer response values "AR" typically require running "known" samples on each analyzer to be normalized. More specifically, in one particular method of normalizing analyzer responses, a target analyzer response value for a given electrolyte, slide lot, and sample electrolyte concentration is first assigned. Then, using that given slide lot, the samples, which have different, but known electrolyte concentrations, are run on the analyzer to be normalized, in order to determine an uncorrected analyzer response for each sample. Multiple runs may be performed, indexed, and averaged with one another to determine an average uncorrected analyzer response for each sample. These uncorrected analyzer responses are then compared to the assigned target analyzer response values that correspond to the given electrolyte concentrations in the samples to determine a specific normalization factor, "$s_{e,c}$," for each of the samples, e.g., for each given electrolyte concentration. This normalization factor, "$s_{e,c}$," is used for all slide lots, although it is only calculated based upon a given slide lot, e.g., the given slide lot mentioned above. Next, the electrolyte concentration-specific normalization factors are averaged (or otherwise correlated) to yield an electrolyte-specific normalization factor applicable to all concentrations of that electrolyte. This normalization factor, "$s_e$," in turn, is used to correct, or "normalize" the analyzer response, e.g., according to:

$$AR_{e,corr} = \frac{AR_e}{s_e} \qquad \text{EQ 2}$$

This corrected, or "normalized" analyzer response, "$AR_{e,corr}$," in conjunction with the slide's lot calibration, is then used to determine the electrolyte concentration of a specific electrolyte in an "unknown" sample.

Although the above-described normalization process, and similar test-based normalization processes, correct for a number of sources of variability, e.g., dispensed volume variation, incubation temperature variation, and timing variation, such processes also introduce a number of additional sources of variability, including: accurate determination of the target analyzer response values, accuracy of the sample concentrations, and the applicability to all slide lots of a single normalization factor determined for one slide lot. Further, the above-described methods also require that multiple samples be run on each analyzer to be normalized in order to determine the normalization factor used to normalize the analyzer response Therefore, a need exists to develop a more efficient and more accurate method for normalizing analyzer response values in fluorometry.

It has been found that a major source of variability in fluorometry for electrolyte detection results from variation in wavelength characteristics of the filter fluorometer. Further, it has been found that accounting for these wavelength-based variations alone (and not considering the other sources of variation discussed above: dispensed volume variation, incubation temperature variation, and timing variation) yields better overall precision, e.g., less analyzer-to-analyzer variation, as compared to slide-based normalization methods, such as those described above. However, producing filters and source(s) (e.g., LED(s)) for use in the analyzers that are optimized to the required individual analyzer accuracy such that wavelength variation is reduced to insignificant levels would significantly increase the costs associated with the manufacture and qualification of such analyzers. It would therefore be desirable to provide a method of wavelength-based normalization for reducing analyzer-to-analyzer variation in fluorometry.

SUMMARY

A method of normalizing an analyzer response value of a filter fluorescence analyzer is provided in accordance with one embodiment of the present disclosure. The method includes measuring an excitation irradiance vs. wavelength spectrum (hereafter, simply "excitation spectrum") of the analyzer as well as sample emission sensitivity vs. wavelength spectrum (hereafter, simply "emission sensitivity spectrum") of the analyzer. A normalization factor is determined based at least in part upon the excitation spectrum of the analyzer and the emission sensitivity spectrum of the analyzer. A sample is then analyzed, i.e., run through the analyzer, to obtain an uncorrected analyzer response value. A normalized analyzer response value can then be determined based at least in part upon the uncorrected analyzer response value and the normalization factor.

In one embodiment, the analyzer excitation spectrum is measured using a spectrometer, while the analyzer emission sensitivity spectrum is measured using a monochromator.

In another embodiment, the normalization factor is determined in accordance with a target normalization factor. Further, the normalization factor may be determined in accordance with one or more wavelength characteristic functions of the analyzer excitation spectrum and/or one or more wavelength characteristic functions of the analyzer emission sensitivity spectrum.

In accordance with another embodiment of the present disclosure, a method of normalizing an analyzer is provided. The method includes measuring an excitation spectrum of the analyzer and determining one or more wavelength characteristic functions of the excitation spectrum of the analyzer. The method further includes measuring an emission sensitivity spectrum of the analyzer and, similarly, determining one or more wavelength characteristic functions of the emission sensitivity spectrum of the analyzer. A normalization factor is then determined based at least in part upon the wavelength characteristic function(s) of the excitation spectrum and the wavelength characteristic function(s) of the emission sensitivity spectrum. The normalization factor, as can be appreciated, is used to normalize an analyzer response value of the analyzer.

In one embodiment, the excitation spectrum of the analyzer is measured to obtain a data set of relative (scaled) irradiance as a function of wavelength. Similarly, the emission sensitivity spectrum of the analyzer may be measured to obtain a data set of analyzer signal to scaled (relative) input irradiance as a function of wavelength.

In another embodiment, the wavelength characteristic function(s) of the analyzer excitation spectrum include a wavelength centroid function, a function representing an area under a portion of the excitation spectrum, the relative irradiance at a predetermined wavelength, a function representing a wavelength at which a relative irradiance exceeds a first predetermined value, and a function representing a wavelength at which the relative irradiance falls below a second predetermined value. The wavelength characteristic function(s) of the analyzer emission sensitivity spectrum may include similar functions.

In yet another embodiment, the normalization factor is determined in accordance with one (or more) of a plurality of wavelength characteristic functions of the analyzer excitation spectrum and/or one (or more) of a plurality of wavelength characteristic functions of the analyzer emission sensitivity spectrum. The one (or more) functions are selected by comparison to a target normalization factor.

Similarly as in the previous embodiment, the analyzer excitation spectrum may be measured using a spectrometer, while the analyzer emission sensitivity spectrum may be measured using a monochromator.

In still yet another embodiment, a set of normalization factors is determined. In such an embodiment, each normalization factor corresponds to a different sensor, e.g., the active component of a slide, to be detected by the analyzer. Further, the normalization factor for each sensor is determined in accordance with one (or more) fitting parameter(s) specific to that sensor.

In accordance with still another embodiment of the present disclosure, a method of normalizing an analyzer in accordance with a specific sensor to be detected by the analyzer is provided. The method includes measuring excitation and emission sensitivity spectra of the analyzer and excitation and emission spectra of the sensor. A first parameter based at least in part upon the overlap of the excitation spectrum of the analyzer and the excitation spectrum of the sensor is determined. A second parameter based at least in part upon an overlap of the emission sensitivity spectrum of the analyzer and the emission spectrum of the sensor is determined. A normalization factor is then determined based at least in part upon the first parameter and/or the second parameter. The normalization factor, as in the previous embodiments, is used to normalize an analyzer response value of the analyzer and the sensor.

In one embodiment, both an early excitation spectrum of the sensor and a late excitation spectrum of the sensor are measured. Similarly, both an early emission spectrum of the sensor and a late emission spectrum of the sensor may be measured. In such an embodiment, the first parameter is a ratio of the overlap of the excitation spectrum of the analyzer with the late excitation spectrum of the sensor divided by the overlap of the excitation spectrum of the analyzer with the early excitation spectrum of the sensor.

In another embodiment, the second parameter is a ratio of the overlap of the emission sensitivity spectrum of the analyzer with the late emission spectrum of the sensor divided by the overlap of the emission sensitivity spectrum of the analyzer with the early emission spectrum of the sensor.

In still another embodiment, the excitation spectrum of the sensor and/or the emission spectrum of the sensor are measured to obtain a data set of fluorescence intensity as a function of excitation wavelength and/or fluorescence intensity as a function of emission wavelength, respectively.

In yet still another embodiment, one or more fitting parameters specific to the interaction of the sensor spectra with the analyzer spectra are used in calculating the normalization factor of that sensor. Further, a target normalization factor may be used in calculating the normalization factor of a particular sensor.

BRIEF DESCRIPTION OF THE DRAWINGS

Various embodiments of the present disclosure are described herein with reference to the drawings, wherein.

DETAILED DESCRIPTION

Figure 1:
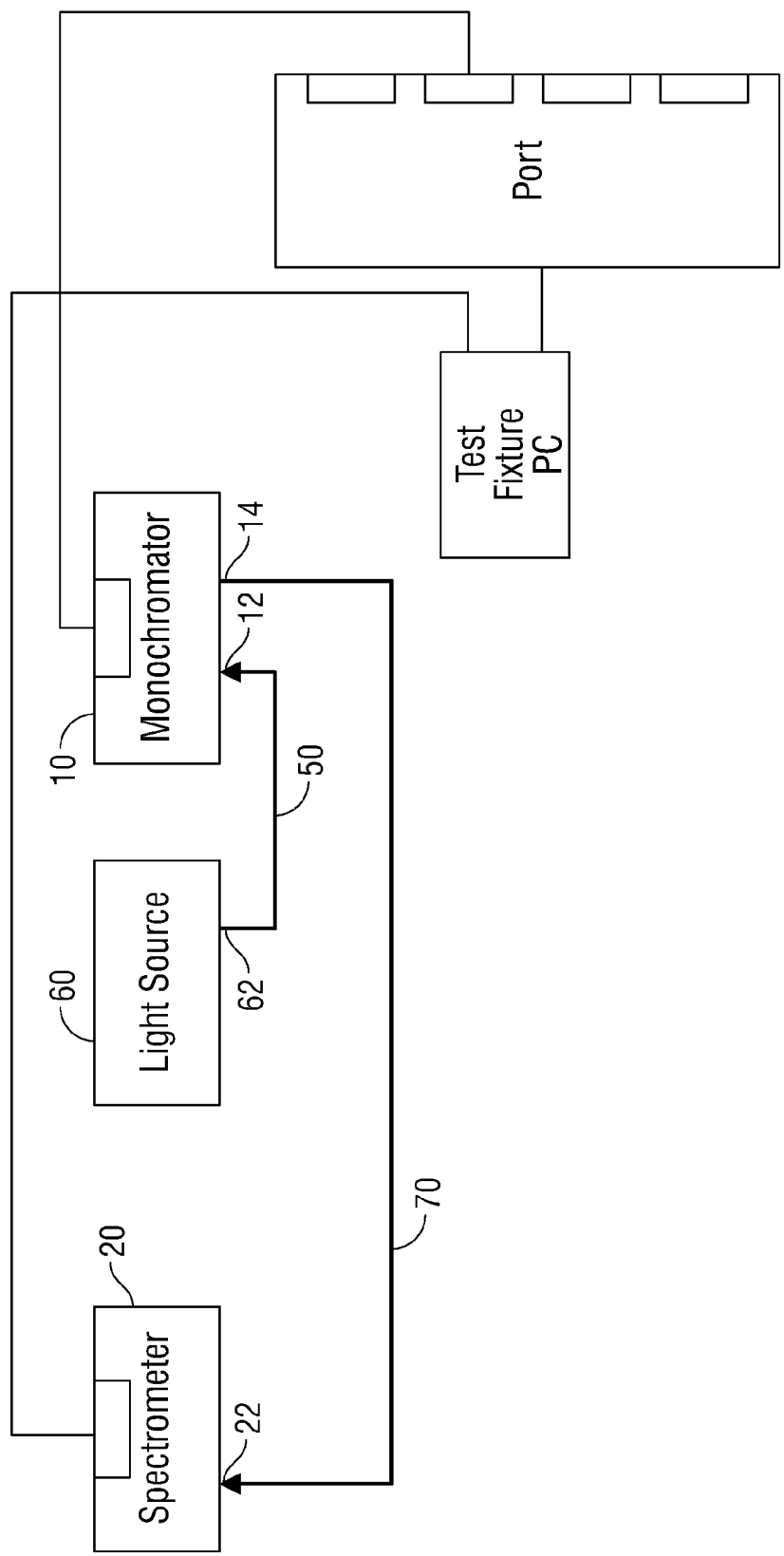
FIG. 1 is a schematic illustration of a configuration for calibrating a monochromator for module emission sensitivity spectrum measurement.

Chemical analyzers, such as those disclosed in commonly-owned, co-pending U.S. Patent Application Publication No. 2010/0254854, the entire contents of which are hereby incorporated by reference herein, measure and analyze optical characteristics of a sample to determine the presence and/or concentration of specific molecules in the sample. In one particular example, chemical analyzers are used to illuminate a sample in order to measure the fluorescence intensity of the sample to determine the concentration of specific molecules, e.g., electrolytes, in the sample. This process is generally referred to as fluorometry.

Although the present disclosure is described with specific reference to electrolyte detection, it is envisioned that the present disclosure may similarly be applied to fluorometry in general. In the following description, the terms "module" and "analyzer" are generally meant to both describe a fluorescence detection system, e.g., the "analyzer" referring to the system as a whole and the "module" referring to the fluorescence detection portion thereof, and, thus, are used generally interchangeably hereinbelow. Further, for purposes of brevity, the term "slide" is meant to include both the slide itself and the sensor, fluorophore, or other electrolyte detector contained thereon. The slide's lot calibration represents a specific calibration factor or function specific to that set of slides. The slide's lot calibration may be provided by the manufacturer of the slides, e.g., in the form of a look-up table, or may be independently calculated. However, the specific calibration of such is not central to the present disclosure and, thus, will not be described herein.

As will be described in greater detail below, the present disclosure relates to wavelength-based methods of normalizing analyzer response values, e.g., the fluorescence intensity readings from the fluorescence detection module of the analyzer, in order to provide more accurate electrolyte concentration readings and to reduce variability in electrolyte concentration readings from analyzer-to-analyzer. These normalized fluorescence readings, in accordance with the slide's lot calibration, are then used to determine the concentration of a specific electrolyte within the sample. As can be appreciated, the presently disclosed normalization methods help reduce the effects of bias that a specific module (or group of modules) of an analyzer may have on the measured electrolyte concentrations of samples run using that specific module (or group of modules). As such, the presently disclosed wavelength-based normalization methods increase the precision and uniformity of electrolyte concentration measurements across all normalized analyzers. More specifically, the presently disclosed wavelength-based normalization methods use wavelength characteristics of the fluorescence detection module of the analyzer and, in some embodiments, of the electrolyte-specific sensors, e.g., fluorophores corresponding to the particular electrolyte to be detected, in order to determine a normalization factor specific to that analyzer for a given electrolyte to be detected. The analyzer response reading of any sample run using the analyzer may then be used, in accordance with the slide's lot calibration information and the corresponding normalization factor, to more accurately determine the concentration of a specific electrolyte within the sample.

In one embodiment, as will be described in greater detail below, one or more functions of the fluorescence detection module's excitation spectrum characteristics and one or more functions of the module's emission sensitivity spectrum characteristics are used to determine the normalization factor for that particular module. More specifically, in equation form, the electrolyte-specific normalization factor, $s_e$, for a particular analyzer is determined in accordance with the function(s) of excitation spectrum characteristics, $f(\lambda)_{e,ex}$, and emission sensitivity spectrum characteristics, $f(\lambda)_{e,em}$, of the module, generally according to:

$$s_e = c_{e,em} \times f(\lambda)_{e,em} + c_{e,ex} \times f(\lambda)_{e,ex} + c_{e,0} \qquad \text{EQ 3:}$$

where $c_{e,em}$, $c_{e,ex}$, and $c_{e,0}$ are electrolyte-specific fitting parameters for the module emission sensitivity function, $f(\lambda)_{e,em}$, the module excitation function, $f(\lambda)_{e,ex}$, and an offset, respectively.

In another embodiment, as will also be described in greater detail below, the fluorescence detection module's excitation spectrum is overlapped with the excitation spectrum of the specific sensor, e.g., fluorophore, to be detected, and the module's emission sensitivity spectrum is likewise overlapped with the emission spectrum of the sensor, in order to determine the normalization factor of the module. This relationship, or overlap, indicates any overlap bias of a particular module/electrolyte combination due to the fact that wavelength characteristics of different modules overlap differently with different fluorophores to be detected. Mathematically, the electrolyte-specific normalization factor, $s_e$, is determined in accordance with overlapping function(s) of excitation spectrum characteristics of the module, $f(\lambda_i)_{m,ex}$, and the early and late excitation spectrum characteristics of the sensor, or fluorophore, to be detected, $f(\lambda_i)_{e,early,ex}$, $f(\lambda_i)_{e,late,ex}$, respectively, and the overlapping function(s) of emission sensitivity spectrum characteristics of the module, $f(\lambda)_{m,em}$, and the early and late emission spectrum characteristics of the fluorophore to be detected, $f(\lambda_i)_{e,early,em}$, $f(\lambda_i)_{e,late,em}$, respectively, generally according to:

$$s_e = c_{e,1} \times \left( \frac{\sum_{i=1}^{N_{ex}} f(\lambda_i)_{m,ex} \times f(\lambda_i)_{e,late,ex}}{\sum_{i=1}^{N_{ex}} f(\lambda_i)_{m,ex} \times f(\lambda_i)_{e,early,ex}} \right) \times \left( \frac{\sum_{i=1}^{N_{em}} f(\lambda_i)_{m,em} \times f(\lambda_i)_{e,late,em}}{\sum_{i=1}^{N_{em}} f(\lambda_i)_{m,em} \times f(\lambda_i)_{e,early,em}} \right) + c_{e,0} \qquad \text{EQ 4}$$

Where, similar to above, $c_{e,1}$ and $c_{e,0}$ are electrolyte-specific fitting parameters and offsets, respectively. Alternatively, as in the form of equation "EQ 3," above, the excitation and emission spectra overlap ratios may each include a separate fitting parameter, $c_{e,ex}$ and $c_{e,em}$, respectively, so that a weighted sum of the two ratios replaces the product of these two ratios shown above.

The above overview of two exemplary methods for wavelength-based normalization of electrolyte-detection modules is not limited to those equations above. Rather, the equations above are simply exemplary equations used to illustrate an example of how wavelength characteristic functions of the module and/or sensor may be used in determining the normalization factor for a particular module/sensor pair. Each of the two embodiments discussed above will be described in turn in greater detail below.

Calibration

As can be appreciated in view of the forgoing, in order to employ wavelength-based normalization for a particular analyzer (or, more particularly, for the fluorescence detection module thereof) and electrolyte to be detected (or, more particularly, sensor, or fluorophore, for detecting the particular electrolyte), it is necessary to measure certain wavelength characteristics thereof. These wavelength characteristics may include: the excitation (output irradiance) spectrum of the module, the emission sensitivity spectrum of the module, the excitation spectrum of the slide, and/or the emission spectrum of the slide. More specifically, in the first embodiment discussed above, the normalization factors are determined based upon a function (or functions) of the excitation spectrum of the module as well as a function (or functions) of the emission sensitivity spectrum of the module and, thus, both the excitation spectrum and the emission sensitivity spectrum measurements are required. In the second embodiment discussed above, the normalization factors are determined based upon the overlap between the excitation spectrum of the module and the excitation spectrum of the slide and the overlap between the emission sensitivity spectrum of the module and the emission spectrum of the slide, and, thus, these measurements are required. The configurations and processes for measuring each of these wavelength characteristics will be described in greater detail below.

Figure 2:
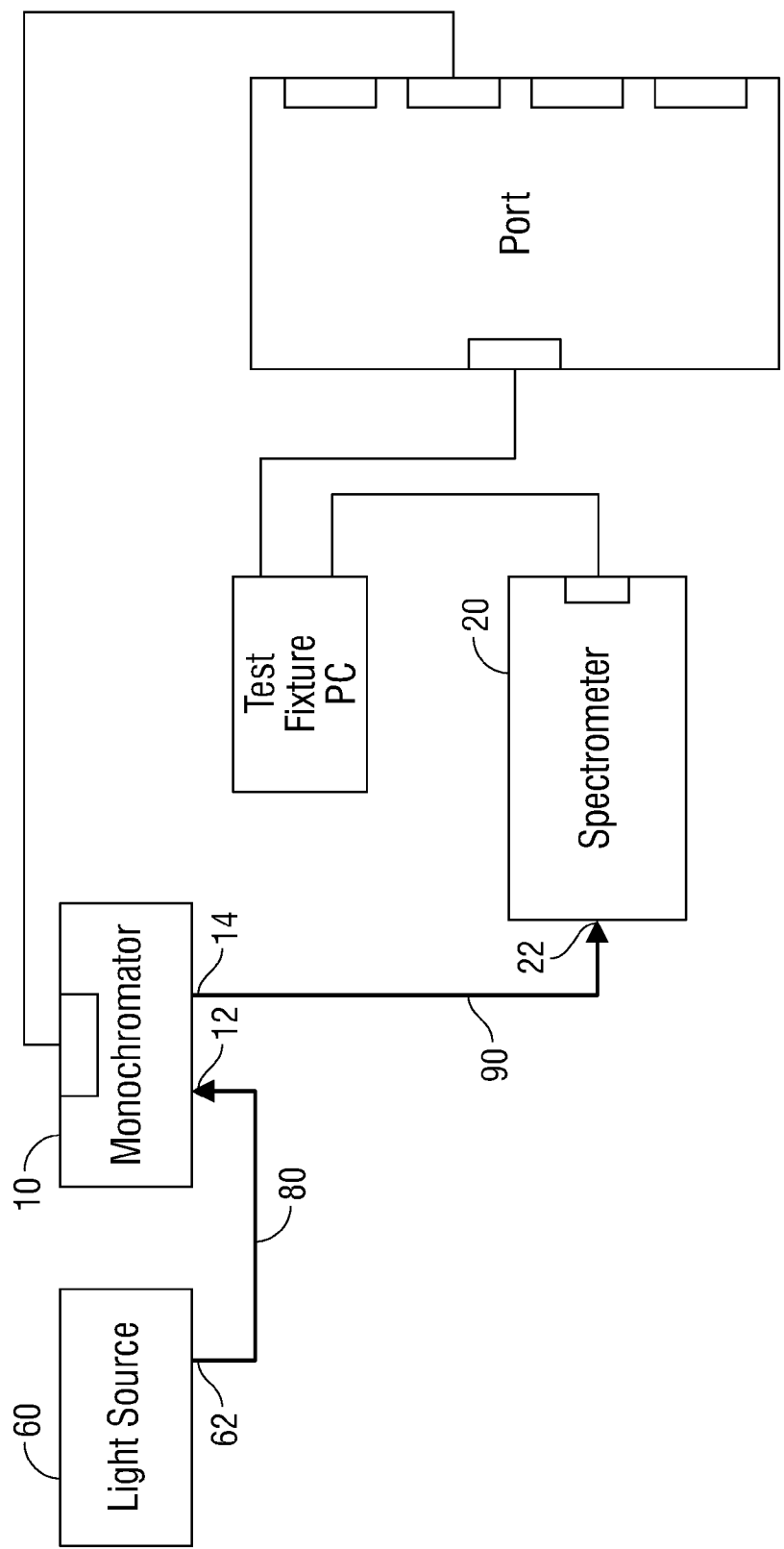
FIG. 2 is a schematic illustration of a configuration for calibrating a monochromator for slide excitation spectrum measurement.

With reference to FIGS. 1 and 2, and as can be appreciated, the accuracy of any spectrum measurement depends, at least in part, on the accuracy of the monochromator 10 and/or spectrometer 20 used to make the measurements. Accordingly, the monochromator 10 and spectrometer 20 must be calibrated prior to obtaining the above measurements to ensure that the spectral characteristics of the module 30 and/or the slide 40 can be accurately measured. More specifically, the monochromator 10 is used in measuring the emission sensitivity spectrum 34 (FIG. 6) of the module 30 and the excitation spectrum 42 (FIG. 8) of the slide 40 and is thus calibrated for each of such measurements. The spectrometer 20, on the other hand, is used for measuring the excitation spectrum 32 (FIG. 4) of the module 30 and the emission spectrum 44 (FIG. 10) of the slide 40, as well as for calibrating the monochromator 10 (FIGS. 1 and 2).

Initially, the spectrometer 20 is calibrated. More specifically, the spectrometer 20 is calibrated for wavelength accuracy, linearity of response, and irradiance sensitivity. The spectrometer 20 used for module excitation and slide emission spectrum measurements may be the Ocean Optics HR2000+ Spectrometer and associated SpectraSuite Spectrometer Operating Software, both available from Ocean Optics, Inc. of Dunedin, Fla., USA, although other suitable spectrometers may also be used. The aforementioned SpectraSuite Software provides procedures for and facilitates calibration of the spectrometer 20 for wavelength accuracy, linearity of response, and irradiance sensitivity. The wavelength accuracy calibration process synchronizes the wavelength positions reported by the spectrometer 20 with well-characterized mercury and argon emission lines. Linearity calibration, on the other hand, is performed to help ensure that, for any given wavelength, the response will scale linearly, e.g., such that a doubling of the irradiance will double the response (signal intensity) produced by the spectrometer 20. Similarly, the irradiance sensitivity calibration is performed to help ensure that the response (signal intensity) produced by the spectrometer 20 at one wavelength can be scaled to the response (signal intensity) produced by the spectrometer 20 at another wavelength, e.g., such that, where the irradiance at a first wavelength and the irradiance at a second wavelength are equal, the signal intensity at both wavelengths is equal.

With the spectrometer 20 calibrated as discussed above, the monochromator 10 may then be calibrated in accordance with the previously-calibrated spectrometer 20. The monochromator 10 used for module emission sensitivity and slide excitation spectrum measurements may be the Ocean Optics MonoScan 2000. While this monochromator is calibrated by its manufacturer, "dependent" calibration of the monochromator 10 has been found to assure a more traceable, and more accurate, calibration of the system, e.g., the monochromator 10 and the spectrometer 20, as a whole, and, thus, produces more accurate measurements as compared to an "independent" calibration of the monochromator 10. As can be appreciated, the calibration of the monochromator 10, which will be described below, provides the data necessary to correlate the step positions of the monochromator 10 to its output dispersion band centroid wavelengths and also allows the detector counts of the module 30 (see FIG. 5) or photomultiplier tube 100 (see FIG. 7) to be scaled, or adjusted, in accordance with the relative irradiance provided by the monochromator 10 and light source 60 at that specific wavelength for which the detector counts were obtained. The monochromator 10 is calibrated first for module emission sensitivity (FIG. 1), in order to obtain module emission sensitivity spectrum measurements, and then for slide excitation (FIG. 2), in order to obtain slide excitation spectrum measurements (although the order may be reversed).

Referring now to FIG. 1, the configuration for calibrating the monochromator 10 for module emission sensitivity spectrum measurements is shown. As shown, the 0.3 mm fiber 50 is coupled between the output 62 of the broadband light source 60 and the input 12 of the monochromator 10 to provide unfiltered light to the monochromator 10. The output 14 of the monochromator 10, in turn, is coupled to the input 22 of the spectrometer 20 via the emission test 0.4 mm fiber 70 such that the spectrometer 20 can read the output dispersion bands of the monochromator 10. The 0.3 mm fiber 50 and the emission test 0.4 mm fiber 70 are the same as those to be used during the module emission sensitivity spectrum measurements, discussed below, such that any bias introduced by the fibers 50, 70 is substantially eliminated.

With continued reference to FIG. 1, during calibration, the spectrometer 20 reads the output dispersion bands of the monochromator 10, e.g., the spectrometer 20 provides relative irradiance values as a function of wavelength for each incremented step position of the monochromator 10. Using this data, as will be described below, monochromator step positions are wavelength-calibrated in, e.g., nanometer (nm) units. Further, the spectrometer data is also used to scale, or adjust the detector counts produced by the module 30 at a given monochromator wavelength to account for the relative output irradiance produced by the monochromator 10 and light source 60 at that wavelength. In other words, this data provides the information necessary to correlate the module 30 detector count values of the analyzer into relative irradiance sensitivity values.

In order to calibrate the monochromator 10, the dispersion band spectrum produced by the monochromator 10 is obtained using the spectrometer 20. More particularly, the monochromator 10 is driven, in approximately 10 nm intervals (although other intervals are contemplated), substantially along the wavelength range to be calibrated and the spectrometer 20 is used to obtain the dispersion band spectrum data at each interval therefrom. Each band spectrum is represented as relative irradiance vs. wavelength (in nm) ordered pairs.

Next, each dispersion band spectrum is least-squares fitted to an un-normalized Gaussian function to determine a band centroid, $\lambda_0$, a band maximum, $l_0$, and a bandwidth parameter, $\sigma$, for each band. The monochromator step positions used are, in turn, then least-squares fitted to the corresponding Gaussian-fitted band centroids, $\lambda_0$, determined above, by a cubic equation.

Although the dispersion bands obtained in this way are substantially Gaussian, they are not perfectly Gaussian and, thus, correction is required. More specifically, it has been found that the band maximum value estimates, $l_0$, are too high. To compensate for this, all data points within +/−1 nm of the band centroids, $\lambda_0$, for each dispersion band spectrum are averaged; the averages of these values are then reassigned as the band maximum values, $l_0$, for the particular dispersion band spectrum.

Next, these monochromator dispersion band maxima, $l_0$, are least-squares fitted to the previously determined band wavelength centroids, $\lambda_0$, by another cubic equation, to determine the relative irradiance output of the monochromator 10 and source 60 as a function of wavelength.

Finally, an output correction function is determined for converting the detector count values to relative irradiance values. The output correction function may be as follows:

$$g(\lambda) = \frac{\alpha_0 + \alpha_1 \lambda_{low} + \alpha_2 \lambda_{low}^2 + \alpha_3 \lambda_{low}^3}{\alpha_0 + \alpha_1 \lambda + \alpha_2 \lambda^2 + \alpha_3 \lambda^3} \quad \text{EQ 5}$$

where $\lambda_{low}$ is the lowest wavelength in the monochromator calibration and the $\alpha$ values are the cubic equation fitting parameters. Using this calibration function, $g(\lambda)$, the module 30 detector count values can be scaled to relative irradiance sensitivity values, e.g., via multiplying by $g(\lambda)$, for module emission sensitivity spectrum measurements.

However, even if the monochromator 10 is accurately calibrated, e.g., as described above, it remains important to ensure that, upon start-up, the monochromator 10 is consistently driven to a set "home" position. As can be appreciated, if the monochromator 10 is not consistently set to the same "home" position each time the monochromator 10 is initialized, the wavelength positions obtained by driving the monochromator's wavelength dispersion grating will vary. In other words, while the monochromator's step size is accounted for in the above-described calibration, if the monochromator 10 does not start from the same "home" position after each start-up, the wavelength values associated with the steps will be shifted by the difference between the actual starting position and the "home" position.

In order to correct for such variability, a "soft home" process is implemented during start-up of the monochromator 10. More specifically, at each start-up, the monochromator grating (not explicitly shown) is driven out of its initial position by a pre-determined number of steps and is then returned to the initial position. This procedure helps ensure that the initial, or start-up position of the monochromator 10 corresponds to a consistent "home" position. Thereafter, the monochromator 10 may be accurately driven to the desired wavelength position.

Two other monochromator wavelength inaccuracy mitigations are also implemented to ensure accurate calibration of the monochromator 10. First, motor backlash is eliminated by driving the monochromator 10 to a position before its starting wavelength, i.e., to a lower value than the starting wavelength, prior to driving the monochromator 10 to the starting wavelength. The wavelength may then be scanned upward to reach the desired starting wavelength. Second, the monochromator calibration process described above is repeated multiple times, e.g., three times. The results from each calibration are then combined to determine the wavelength and irradiance sensitivity calibrations.

Turning now to FIG. 2, the configuration for calibrating the monochromator 10 for slide excitation spectrum measurements is shown. The configuration for calibration of the monochromator 10 for slide excitation spectrum measurements is similar to the configuration for calibrating the monochromator 10 for module emission sensitivity spectrum measurements (see FIG. 1). However, rather than using the 0.3 mm fiber 50 to couple the light source 60 and monochromator 10 and the 0.4 mm emission test fiber 70 to couple the monochromator 10 and the spectrometer 20, the 0.6 mm fiber 80 is coupled between the output 62 of the light source 60 and the input 12 of the monochromator 10 to provide unfiltered light to the monochromator 10, while the output 14 of the monochromator 10 is coupled to the input 22 of the spectrometer 20 via the excitation test 1.0 mm fiber 90. Similarly as described above, these fibers 80, 90 are the same as those to be used during the slide excitation spectrum measurements such that any bias due to the fibers 80, 90 is substantially eliminated. These larger core diameter fibers 80, 90 are used for slide fluorescence excitation spectrum measurements to ensure that the fluorescence signal is strong enough for reproducible measurement.

The data produced by the spectrometer 20 is then used, similarly as above, to correlate the step positions of the monochromator 10 to its output wavelength centroids (e.g., nanometers) and to scale the photomultiplier tube 100 (see FIG. 7) detector count values according to the relative input irradiance from the monochromator 10 and source 60. The source 60 (and its intensity setting) used for the monochromator 10 calibrations is also used in obtaining module emission sensitivity spectra or slide excitation spectra.

Measurement

FIGS. 3-10 show the configurations for measuring the various wavelength characteristics of the module 30 and slide 40 and sample spectra 32, 34 and 42, 44, respectively, for each of such measurements. Each of these configurations will be discussed in greater detail below. However, it is envisioned that other suitable configurations may also be employed, as the configurations shown in FIGS. 3, 5, 7 and 9 are only exemplary. Likewise, the sample spectra shown in FIGS. 4, 6, 8 and 10 are just that, samples of typical measured spectra. Further, the monochromator calibration configurations discussed above (FIGS. 1-2) may also be modified, as desired, and are similarly only exemplary configurations.

Figure 3:
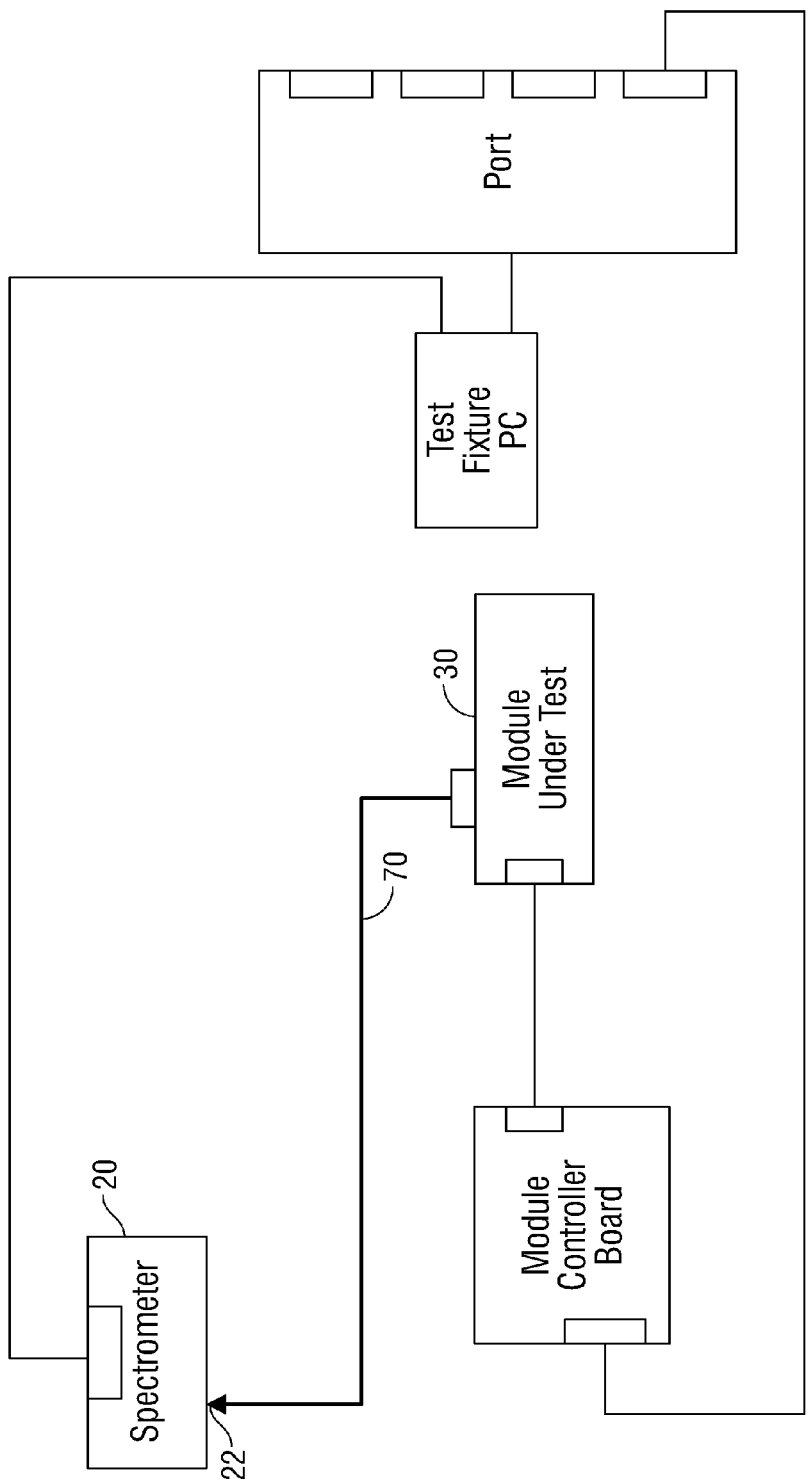
FIG. 3 is a schematic illustration of a configuration for measuring an excitation spectrum of a module under test.

As shown in FIG. 3, the configuration for measuring the excitation spectrum of a given module 30 under test is shown. As shown, a 0.4 mm excitation test fiber 70 is coupled between the module 30 and a spectrometer 20. For obtaining the module excitation spectrum, the excitation test fiber 70 is approximately centered on the optical axis of the module 30. This ensures that the wavelengths received by the excitation test fiber 70 provide a consistent module-to-module approximation of the wavelengths that the slide 40 would receive during testing. Because the fluorescence excitation intensity of the module 30 is high, the proximal end of fiber 70 may be spaced back from the typical location at which slide 40 is read. Further, the proximal end of fiber 70 is located perpendicularly to the optical axis of module 30. The measured excitation spectrum 32 (FIG. 4) of the module 30 provides the relative excitation irradiance at each wavelength. More specifically, this excitation spectrum 32 (FIG. 4) is used to compile data in the form of a (wavelength, relative irradiance) ordered pair for each wavelength in the range tested, typically in 0.2 nm increments. Further, if necessary, this data may then be filtered, e.g., via Gaussian smoothing, boxcar averaging, or any other suitable method. As can be appreciated, and as will be described in greater detail below, this data indicates the presence of any biases in the module 30 so that these biases may be accounted for in the determination of the normalization factor specific to that module 30.

Figure 4:
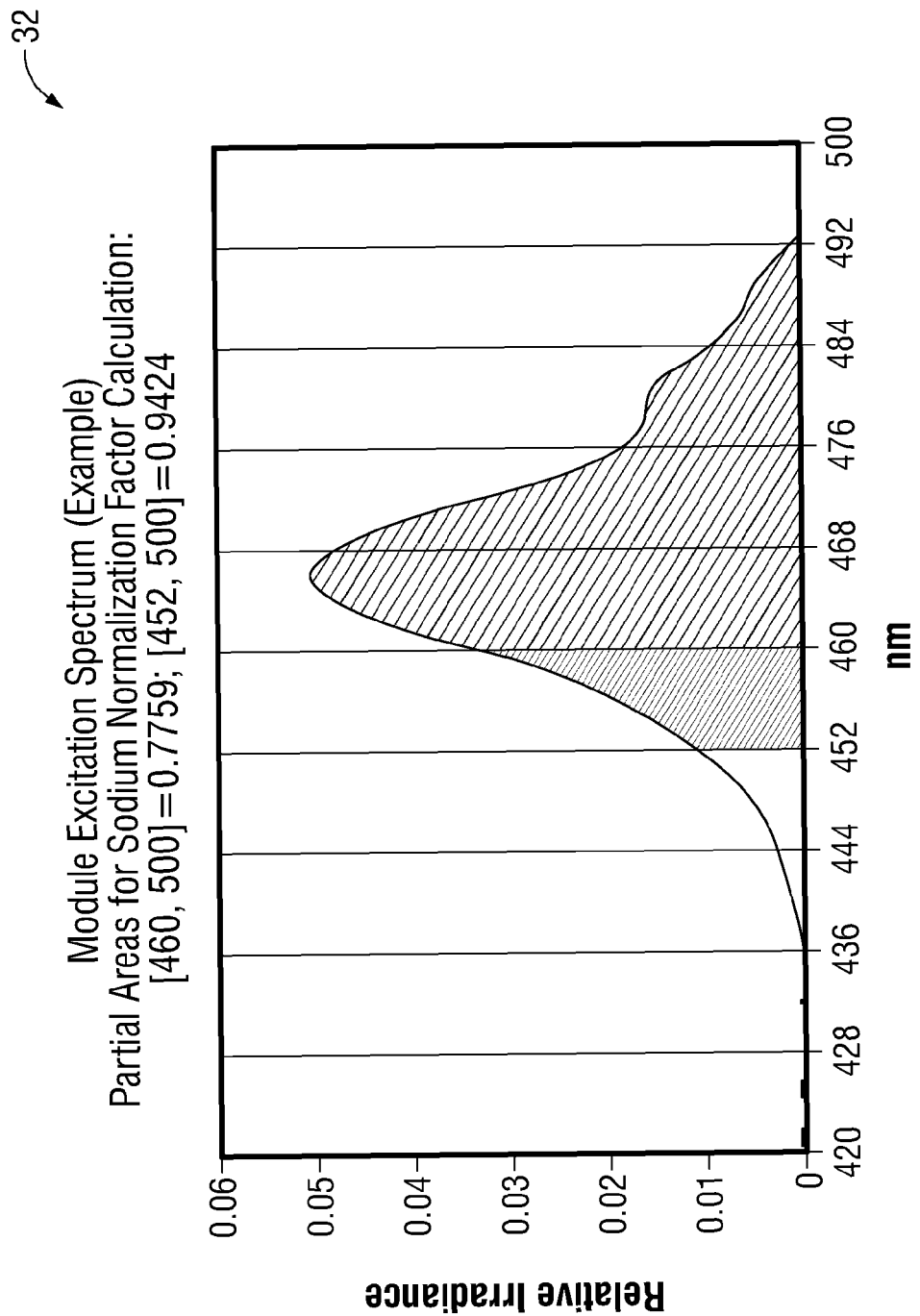
FIG. 4 is an example module excitation spectrum.

With reference to FIG. 4, in conjunction with FIG. 3, a sample module excitation spectrum 32 is shown. This module excitation spectrum 32, as shown in FIG. 4, reveals a blue wavelength band with a peak typically in the range of about 460 nm to about 470 nm. The LED source (not explicitly shown) of the module 30 and the filters (not explicitly shown) employed in the module 30 work to limit the range of available excitation intensity to within about 430 nm to about 500 nm. The module excitation spectrum 32 shows the light energy provided by the module at a range of wavelengths. More specifically, the module excitation spectrum 32 represents the energy available to be absorbed by the slide 40 during the fluorescence detection process for measuring the concentrations of electrolytes in a sample. FIG. 4 also shows two shaded areas under the spectrum curve corresponding to two exemplary pre-determined wavelength ranges, 452 nm to 500 nm and 460 nm to 500 nm. As will be described in greater detail below, in this example, these areas are ultimately used in order to estimate the normalization factor to be employed for sodium slide tests.

Figure 5:
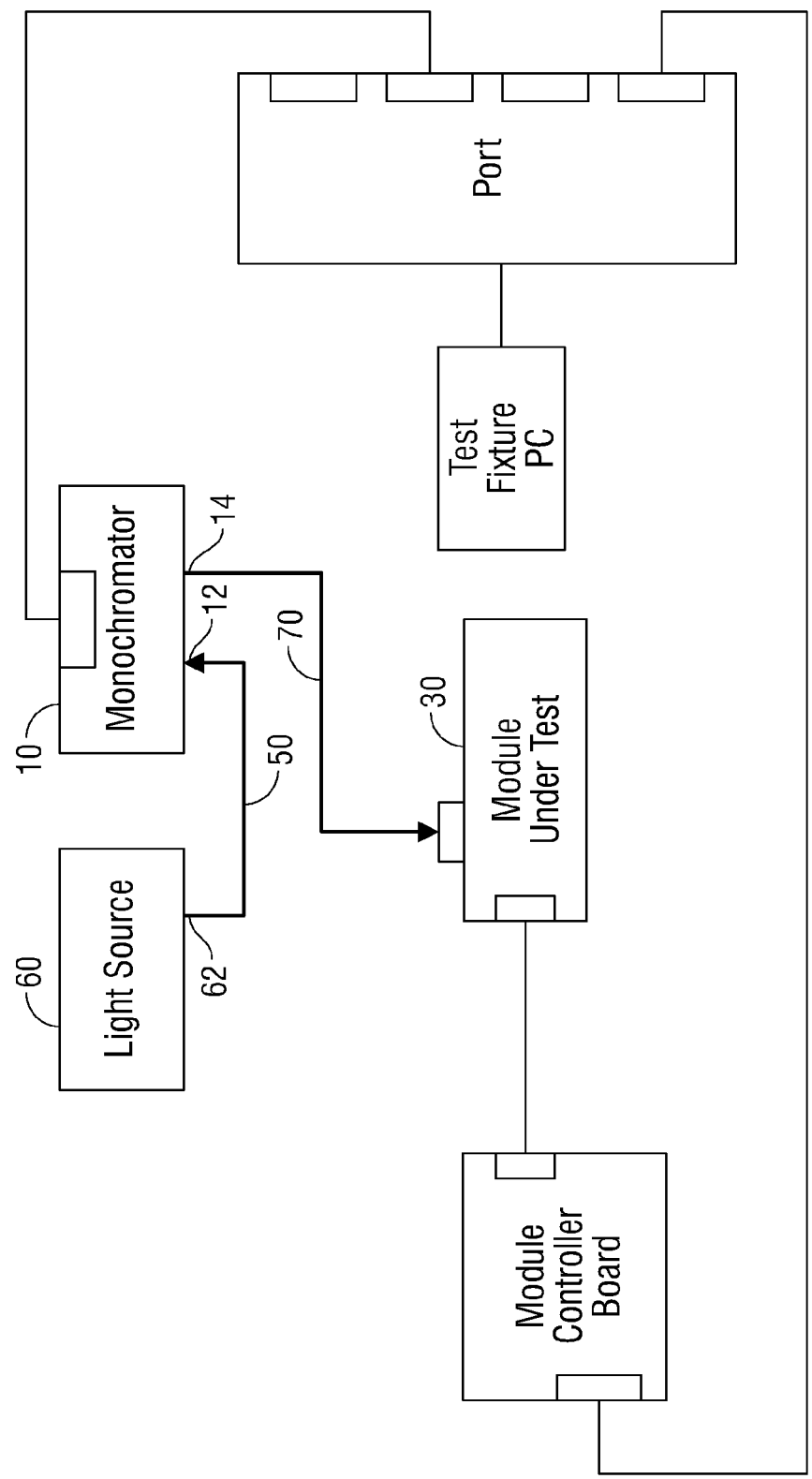
FIG. 5 is a schematic illustration of a configuration for measuring an emission sensitivity spectrum of the module.

With reference to FIG. 5, measurement of the emission sensitivity spectrum 34 (FIG. 6) of the module 30 will be described. Prior to measuring the emission sensitivity spectrum 34 (FIG. 6) of the module 30, the monochromator 10 is calibrated for such measurement, as described above. The same 0.3 mm fiber 50 used in the calibration of the monochromator 10 remains coupled between the broadband light source 60 and the monochromator 10 for providing unfiltered light to the monochromator 10. During each test run, the monochromator 10, in turn, produces a narrow band of light that is transmitted through a 0.4 mm emission test fiber 70 (the same fiber 70 used in the calibration of the monochromator 10) coupled between the monochromator 10 and the module 30. The proximal end of emission test fiber 70 is approximately centered on and perpendicular to the optical axis of module 30 for the testing. Further, the proximal end of the emission test fiber 70 is positioned at approximately the same distance from module 30 as slide 40 is to be located when the module 30 is used to read the fluorescence of the slide 40. This positioning helps to ensure that the wavelengths received from the emission test fiber 70 are substantially similar to those that are to be received from the slide 40. Typically, the tests are run at 0.2 nm increments across the entire range of wavelengths to be tested. The resulting emission sensitivity spectrum 34 (FIG. 6) as produced by the module 30 is then obtained in the form of (monochromator steps, detector counts) ordered pairs. This data is subsequently scaled to the corresponding (wavelength, relative input irradiance sensitivity) ordered pairs. Similarly as above, the emission sensitivity spectrum data may also be filtered. Further, as can be appreciated, and as will be described in greater detail below, this data indicates the presence of any biases in the module 30 so that these biases may be accounted for in the determination of the normalization factor specific to that module 30.

Figure 6:
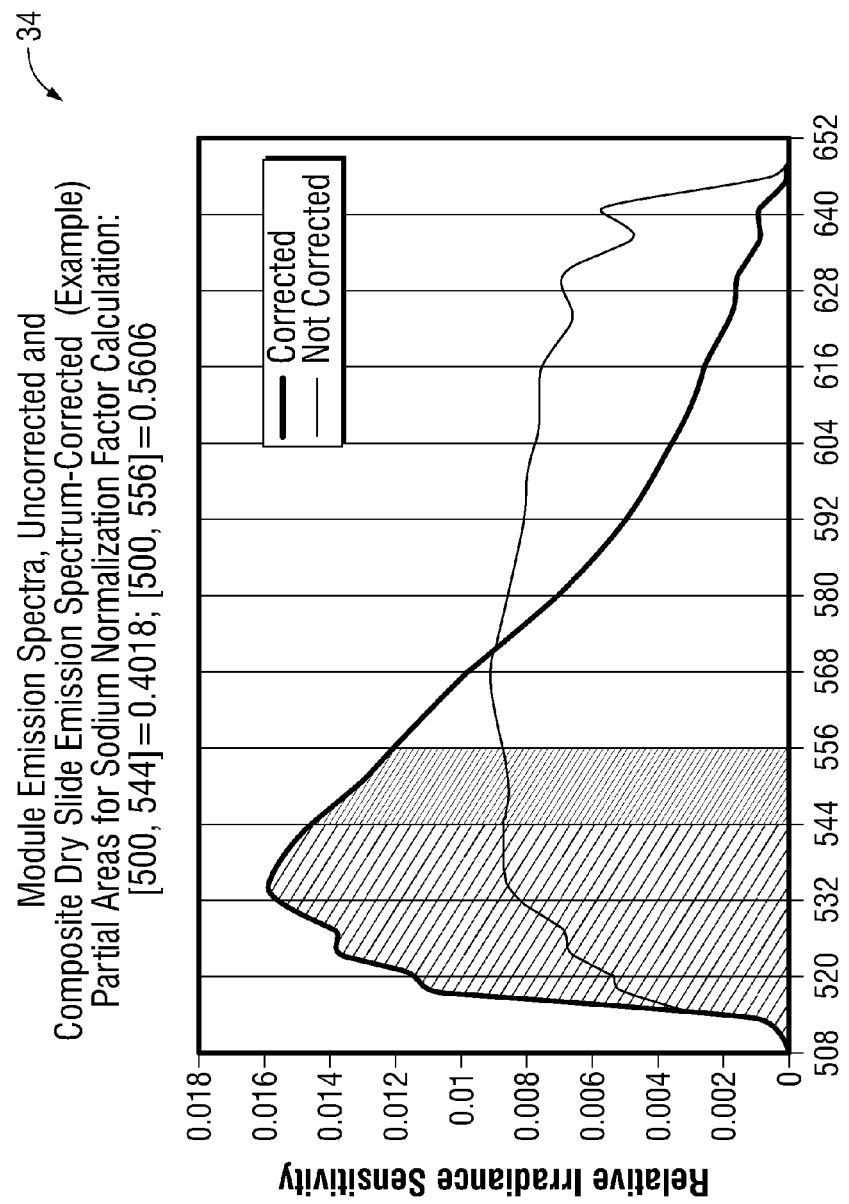
FIG. 6 is an example module emission sensitivity spectrum.

With reference to FIG. 6, a sample module emission sensitivity spectrum 34 is shown. The uncorrected module emission sensitivity spectrum 34 reveals a broad wavelength band of sensitivity spanning a substantial portion of the green, yellow, orange, and red regions of the electromagnetic spectrum. The silicon photodiode detector (not explicitly shown) of the module 30 and the filters (not explicitly shown) employed in the module work to limit the range of light sensitivity to within about 510 nm to about 650 nm. The module emission sensitivity spectrum shows the light energy sensitivity of the module at a range of wavelengths. That is, the module emission sensitivity spectrum represents the emitted slide energy that is detectable by the module during the fluorescence detection process for measuring the concentrations of electrolytes in a sample. FIG. 6 also shows the result of the overlap of this module emission sensitivity spectrum (the "uncorrected spectrum") with a composite (of the sodium, potassium, and chloride electrolytes') dry slide emission spectra to form a "corrected" spectrum. The corrected emission sensitivity spectrum provides decreased sensitivity to variability towards the higher end of the wavelength spectrum, i.e., it is less sensitive with respect to longer wavelengths, as compared to the uncorrected spectrum. By using the corrected module emission sensitivity spectrum, more accurate module normalization factors can be obtained.

FIG. 6 also shows two shaded areas under the corrected emission sensitivity spectrum curve corresponding to two exemplary pre-determined wavelength ranges, 500 nm to 544 nm and 500 nm to 556 nm. These areas, as will be described in greater detail below, are ultimately used in to estimate the normalization factor to be employed for sodium slide tests.

Figure 7:
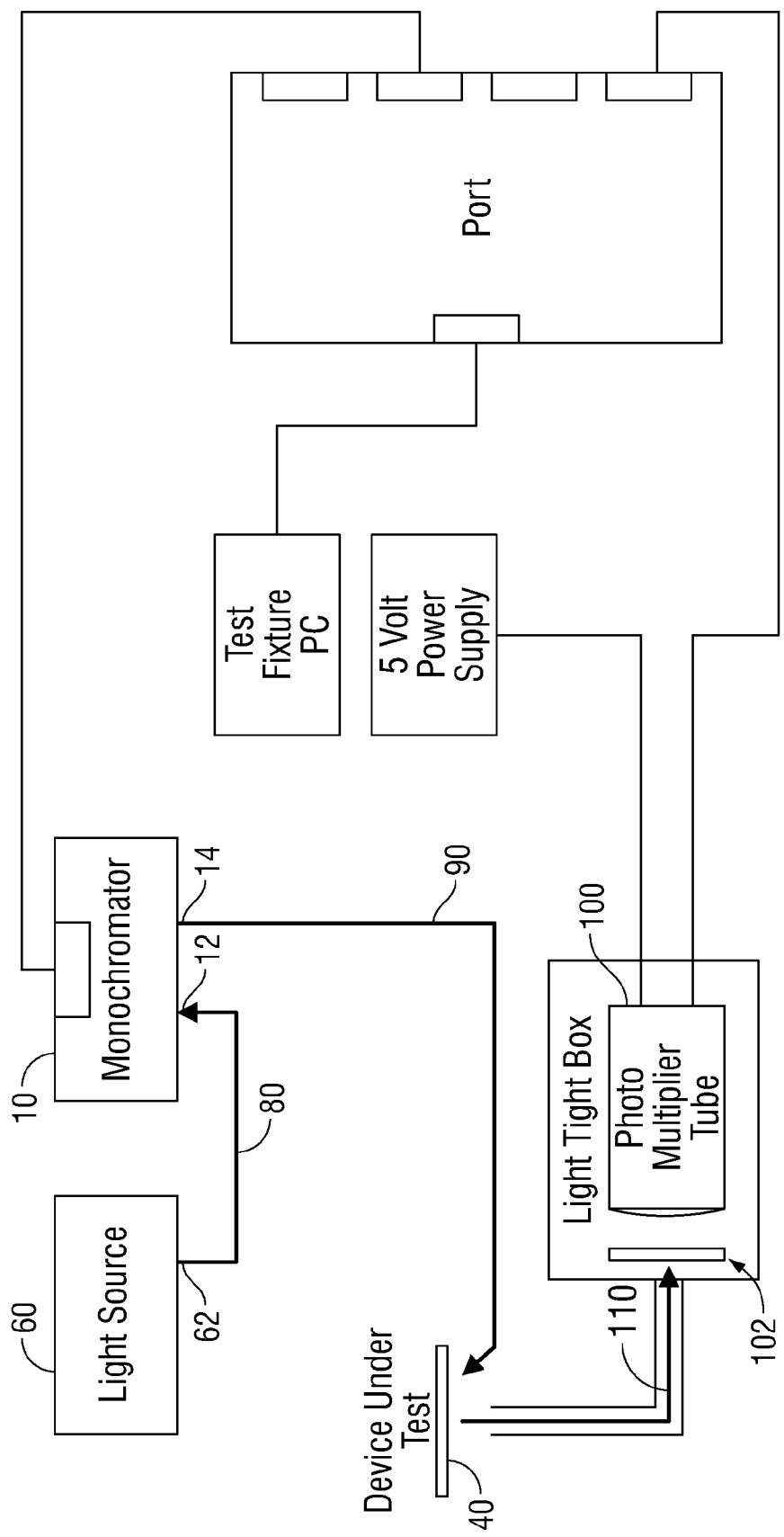
FIG. 7 is a schematic illustration of a configuration for measuring a slide excitation spectrum.

With reference now to FIG. 7, the excitation spectrum 42 (see FIG. 8) of the slide 40 may be overlapped with the excitation spectrum 32 (see FIG. 4) of the module 30 in order to correct for module-to-module and/or slide lot-to-slide lot wavelength differences with specific normalization factors. As shown in FIG. 7, to obtain a fluorescence excitation spectrum of a sample, such as of slide 40, the fluorescence emitted by the sample is detected at a fixed wavelength band while scanning the input (excitation) light wavelengths and recording the detected fluorescence intensity for each wavelength scanned. As can be appreciated, generating a narrow excitation wavelength band of light and transporting it to the slide 40 is inefficient in that only a small fraction of the source intensity is available to excite the fluorescence of the slide 40. Therefore, a sensitive photomultiplier tube 100 is employed to detect the slide fluorescence and is filtered, e.g., using a 550AELP redundant "long pass" filter 102, available from Omega Optical, Inc. of Brattleboro, Vt., USA, to pass only light wavelengths above about 550 nm. Similarly, large core diameter fibers 90 and 110 are used to maximize light throughput. Like the module emission sensitivity measurement (see FIG. 6), the slide excitation spectrum 42 is essentially a sensitivity spectrum, in this case detecting the fluorescence intensity in response to excitation light of known relative (scaled) irradiance and wavelength. The excitation light is delivered at an approximately 45° angle to the slide 40, e.g., via the 1 mm excitation test fiber 90, and the emitted light is detected in general axially alignment with the center of the slide 40, e.g., via 1 mm detection fiber 110.

Figure 8:
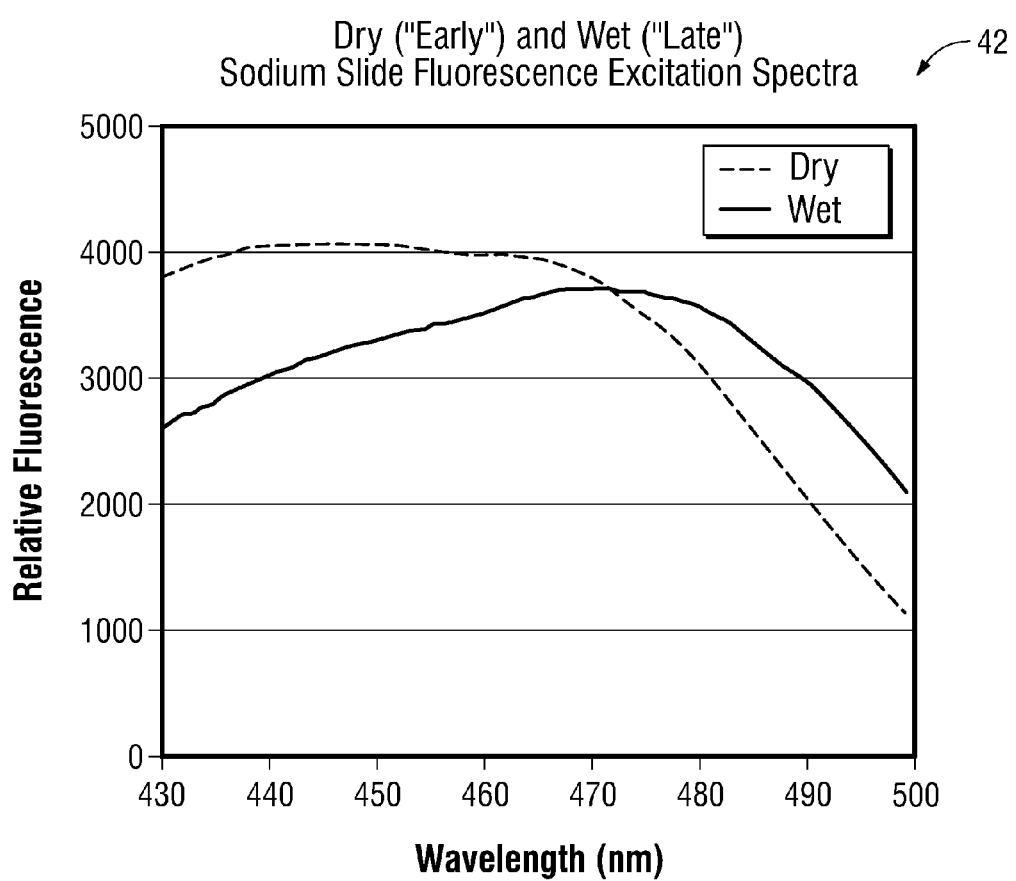
FIG. 8 shows superimposed "early" and "late" excitation spectra for sodium detection slides.

With reference to FIG. 8, an example of sodium sensor "early" and "late" spectra are shown. In order to obtain the "early," or "dry," readings of slides 40 run in the analyzer, readings are obtained at approximately 25 seconds and again at 9 seconds prior to the sample being added. These readings are then averaged to obtain the "dry," or "early" slide reading. At approximately 3 minutes and 14 seconds and again at 3 minutes and 25 seconds after the sample is added to the slide 40, the "wet" slides 40 are once again read by the analyzer and a pair of "late" readings for each slide 40 is obtained. These readings are then averaged to form the "wet," or "late" slide reading. However, it is also envisioned that different time intervals and/or greater or fewer discrete readings may be analyzed, depending on the particular sensor used. For example, the time intervals and the number of readings used for sodium are different from those used for potassium and chloride.

The "early" and "late" slide excitation spectra are obtained at approximately the same time intervals as the "early" and "late" slide readings, discussed above, in order to determine a relationship between the spectra, which interact with the module excitation spectrum, and the module's slide readings, e.g., in order to determine the effect of the spectra on the module's slide readings. This is important because, just as the sample concentration affects the analyzer response, as discussed above with respect to equation "EQ 1," the sample concentration also affects the magnitude of the "late" spectrum at a given time after sample addition, thereby affecting the analyzer response.

Further, as also discussed above with respect to equation "EQ 1," above, the analyzer subtracts the background fluorescence intensity, e.g., the baseline reading, from the early and late readings prior to ratioing them to form the uncorrected analyzer response. Similarly here, the fluorescent background baseline slide spectra are obtained and are subtracted from the early and late spectra. In obtaining these baseline spectra, special sensor slides configured with the same ingredients and production processes as the normal slides, minus the active fluorophore, are used. This same type of "background" sensor slide is used in the analyzer, typically at manufacture or service, to measure background fluorescence intensity for subtraction from the early and late fluorescence readings.

Figure 9:
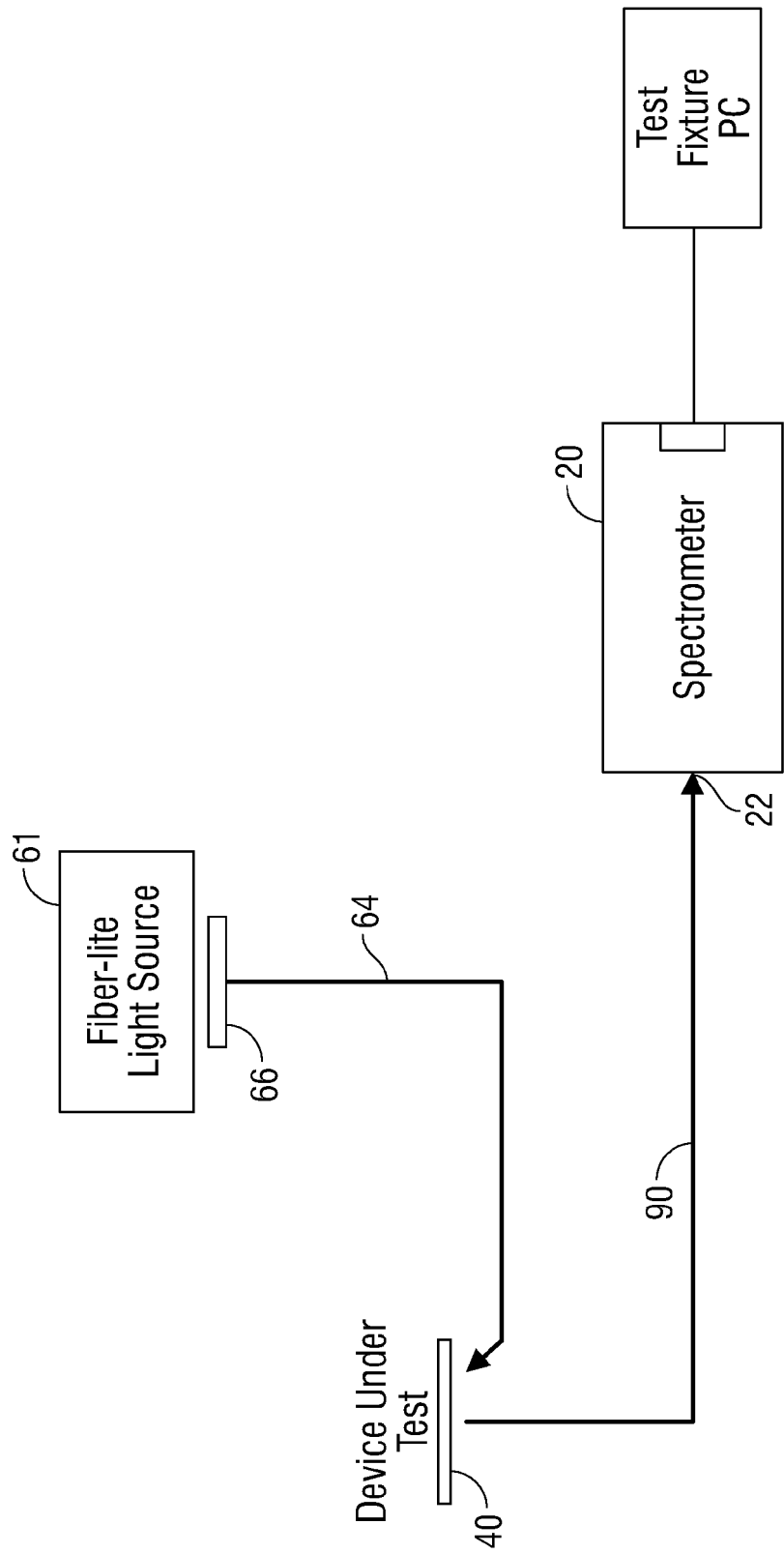
FIG. 9 is a schematic illustration of a configuration for measuring the slide emission spectrum.
Figure 10:
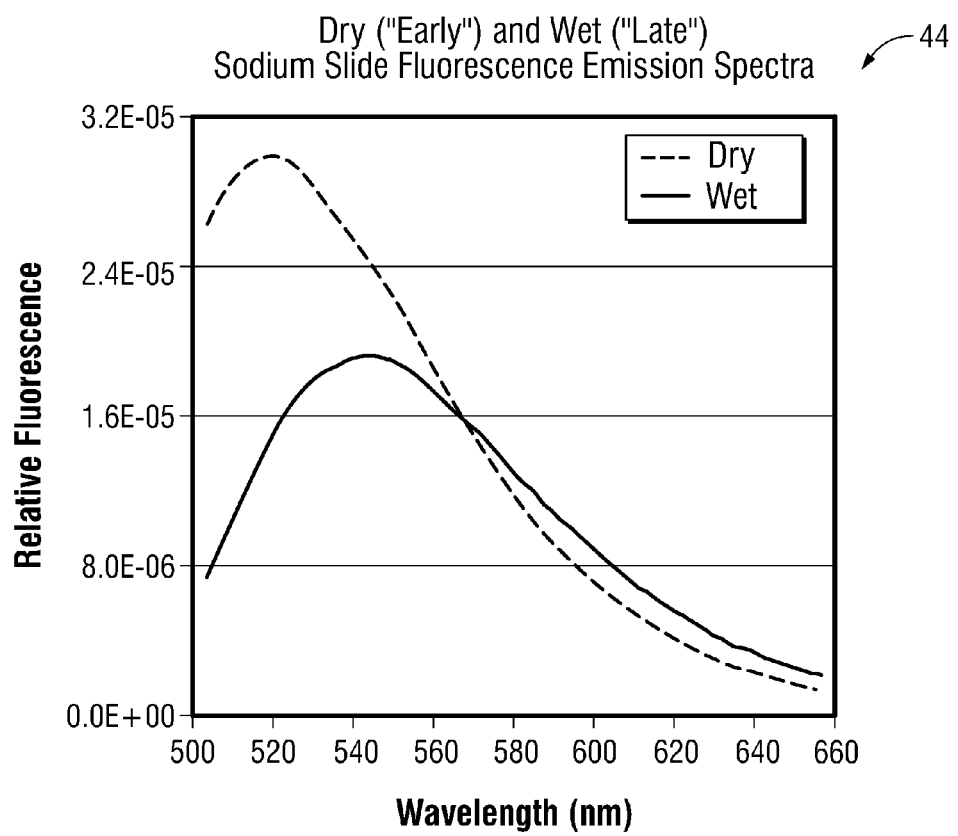
FIG. 10 shows superimposed "early" and "late" emission spectra for sodium detection slides.

With reference to FIGS. 9 and 10, as mentioned above, the emission spectrum 44 of the slide 40 may also be overlapped with the emission sensitivity spectrum 34 of the module 30 (see FIG. 6) to correct for module-to-module and/or slide lot-to-slide lot wavelength differences with specific normalization factors. A fluorescence emission spectrum 44 of a sample, such as of slide 40, consists of recording the fluorescence emitted by the sample at discrete wavelength values over a selected wavelength range, while the input (excitation) light wavelength range and intensity remain fixed. Due to the relatively weak fluorescence intensity and insensitivity of the spectrometer, large core diameter fibers 64 and 90 are used to excite and capture sufficient fluorescence intensity, respectively. A higher intensity source 61, e.g., a Fiber-Lite® High Intensity Fiber Optic Illuminator, available from Dolan-Jenner Industries of Boxborough, Mass., USA, and a short pass (red blocking) filter 66, e.g., a 3RD490SP filter (Omega Optical), provide the fluorescence excitation intensity required for the slide emission spectrum measurement. Again, the excitation light is delivered at an approximately 45° angle to the slide 40, and the emitted light is detected in general axial alignment with the center of the slide 40.

With reference now to FIG. 10, examples of sodium sensor "early" and "late" emission spectra are given. The spectra shown are the results of obtaining "early" and "late" emission spectra at approximately the same times as they are obtained by the analyzer, and subtracting from each the sodium sensor background emission slide spectrum, similarly as discussed above with reference to FIG. 8. As shown in FIG. 10, the two spectra do not have proportionate relative fluorescence to one another; if they did, and the "early" and "late" slide excitation spectra did as well, then the uncorrected analyzer response ratio in equation "EQ 1" would largely correct for analyzer-to-analyzer differences, and a normalization factor would be unnecessary. However, as clearly shown in FIG. 10, the shapes and peak wavelengths of the "early" and "late" bands differ, thus requiring normalization. More specifically, since different module emission sensitivity spectra indicate variable relative sensitivity to the "early" and "late" fluorescence spectra of a given sensor, thus resulting in different analyzer responses, a normalization factor to correct for module-to-module differences is required. Likewise, if the emission spectra of the slide 40 vary from slide lot-to-slide lot, the normalization factor may be calculated to adjust for these differences as well. However, if the "early" and "late" emission spectra remain consistent in form, other than multiplicative scaling differences, which are compensated by slide lot calibration, then the normalization factors need only be applied on a module-to-module basis. Further, it is noted that, although fluorescence intensities below 500 nm and above 660 nm are produced, the module 30 has no sensitivity to fluorescence intensity at wavelengths outside this about 510 nm to about 650 nm range (see FIG. 6) and, thus, the slide emission spectra are only measured within the range shown in FIG. 10.

The slide emission spectrum measurement configuration, e.g., the high-intensity broadband light source 61 (with short pass filter 66) and excitation fiber 64, is calibrated using stable NIST Standard Reference Material 2941 (not shown). The reference material (not shown) is placed with its frosted slide located where the slide 40 would normally be placed. The emission spectrum of the reference material is obtained and compared against the NIST-published reference emission spectrum for this standard. Individual wavelength correction factors are determined by computing the ratio of the NIST reference spectrum divided by the measured emission spectrum of the standard for each wavelength obtained and to be used for slide spectra. Slide emission spectra are then corrected by multiplying the correction factor ratios by the measured emission spectrum on a wavelength-by-wavelength basis.

Target Normalization Factors

In some embodiments, target normalization factors may be determined and are used in accordance with the measured module wavelength characteristics to ultimately determine the normalization factors of each analyzer for a given electrolyte to be detected. Two different methods of determining the target normalization factors for the module will be discussed in turn below, although other suitable methods for determining target normalization factors are also contemplated. Alternatively, it is envisioned that the herein disclosed wavelength-based normalization factors be calculated without reference to a target normalization factor.

In one embodiment, the target normalization factors are determined in accordance with a "standard analyzer" (or group of analyzers). In this embodiment, a plurality of samples having different concentrations is tested. More specifically, for each sample run on the module under test, the electrolyte concentration of the sample is also detected using the standard analyzer. The slide's lot calibration information, and the electrolyte concentration of the sample, as determined by the standard analyzer, are then used to back-correlate a target analyzer response, $AR_{0,e,l,c}$, for each sample. The target normalization factor, $s_{e,c}$, for each concentration, in turn, may then be calculated using the target analyzer response, $AR_{0,e,l,c}$, and the uncorrected analyzer responses, $AR_{e,l,c,i}$ (the analyzer responses from running the sample on the module under test) according to:

$$s_{e,c} = \frac{\sum_{i=1}^{n} AR_{e,l,c,i}}{n \times AR_{0,e,l,c}} \quad \text{EQ 6}$$

As noted previously, e indicates the electrolyte to be detected, l the slide lot, c the electrolyte sample concentration tested, and n the total number of replicate tests, with i indexing the replicates. Typically, these concentration-specific normalization factors, $s_{e,c}$, are averaged to determine the electrolyte-specific (but not concentration-specific) target normalization factor, $s_e$, for the analyzer under test.

In another embodiment, a given sample (or samples) is run on a "training set" of different analyzers, with each analyzer producing an uncorrected analyzer response, $AR_{e,l,c,i}$. These uncorrected analyzer responses are then averaged to produce the target analyzer response, $AR_{0,e,l,c}$. From there, similarly as above, an electrolyte-specific (but not concentration-specific) target normalization factor, $s_e$, for each analyzer is determined.

Armed with the wavelength characteristic measurements and target normalization factors, as determined by either of the methods described above, or any other suitable method, the normalization factors for a given module/fluorophore pair can be determined, as will be described with reference to the embodiments discussed below.

Embodiment 1

Initially, as discussed above, the module excitation spectrum data, relative irradiance as a function of wavelength, $f(\lambda_i)_{m,ex,in}$, is collected as (wavelength, relative irradiance) ordered pairs, and is indexed accordingly. The module emission sensitivity data, detector counts as a function of monochromator step, is converted to (wavelength, relative irradiance sensitivity) ordered pairs in accordance with the monochromator calibration information discussed above, to yield a relative irradiance sensitivity spectrum as a function of wavelength, $f(\lambda_i)_{m,em,corr}$. This emission sensitivity spectrum may be overlapped with a composite dry slide emission spectrum to minimize the effects of portions of the module emission sensitivity spectrum unimportant for calculating module normalization factors. Further, as mentioned above, both data sets may be filtered. The subscripts m, ex or em, and in or corr indicate, respectively, the specific module, excitation or emission sensitivity, and "input" or "corrected," respectively.

Next, the module excitation spectrum data and module emission sensitivity data is standardized, to substantially remove any random relative intensity calibration error. For example, the module excitation spectrum data may be standardized according to:

$$f(\lambda_i)_{m,ex} = \frac{f(\lambda_i)_{m,ex,in}}{\sum_{i=1}^{N_{ex}} f(\lambda_i)_{m,ex,in}} \quad \text{EQ 7}$$

while the module emission sensitivity spectrum data may be standardized according to:

$$f(\lambda_i)_{m,em} = \frac{f(\lambda_i)_{m,em,corr}}{\sum_{i=1}^{N_{em}} f(\lambda_i)_{m,em,corr}} \quad \text{EQ 8}$$

Alternatively, it may be preferable to mathematically normalize either one of the functions $f(\lambda_i)_{m,ex,in}$ or $f(\lambda_i)_{m,em,corr}$ if the wavelength increments over which the spectra were obtained are not equally-spaced. In either case, the resulting functions $f(\lambda_i)_{m,ex}$ or $f(\lambda_i)_{m,em}$ may be used to compare, respectively, the excitation or emission sensitivity spectra of different modules.

As another alternative, the spectra may be standardized based upon the overlap of the respective excitation spectrum and emission sensitivity spectrum of the module and a standard (typically dry) slide excitation spectrum and emission spectrum. In this embodiment, the standardized spectra are electrolyte-specific. More particularly, the module excitation spectrum data may be standardized according to:

$$f(\lambda_i)_{m,e,ex} = \frac{f(\lambda_i)_{m,ex,in} \times f(\lambda_i)_{dry,e,ex}}{\sum_{i=1}^{N_{ex}} f(\lambda_i)_{m,ex,in} \times f(\lambda_i)_{dry,e,ex}} \quad \text{EQ 9}$$

while the module emission sensitivity spectrum data may be standardized according to:

$$f(\lambda_i)_{m,e,em} = \frac{f(\lambda_i)_{m,em,corr} \times f(\lambda_i)_{dry,e,em}}{\sum_{i=1}^{N_{ex}} f(\lambda_i)_{m,em,corr} \times f(\lambda_i)_{dry,e,em}} \quad \text{EQ 10}$$

These equations ("EQ 9" and "EQ 10") combine the spectrum overlap process with a standardization process, both described above. A preferred method for generating a "corrected," non-electrolyte-specific, composite dry slide emission spectrum's overlap with a module emission sensitivity spectrum was described above.

Using these standardized spectra, $f(\lambda_i)_{m,ex}$ and $f(\lambda_i)_{m,em}$, (or, for the electrolyte-specific standardization, $f(\lambda_i)_{m,e,ex}$ and $f(\lambda_i)_{m,e,em}$) determined above, various characteristics of the spectra can be determined, e.g., the wavelength centroid, the area under portions of the spectrum, the wavelength at which the relative irradiance exceeds or drops below a particular level (or levels), the relative irradiance(s) at a particular wavelength (or wavelengths). These characteristics are then incorporated into one or more functions of such characteristics that are then used in determining the corresponding normalization factor.

For example, by testing various normalization factor equation forms and least-squares optimizing functions of module excitation and emission sensitivity spectra, the following functions and coefficients were determined to be particularly suitable for use in calculating the target normalization factors for a given module:

$$s_{Na,m} = a_{Na,0} + a_{Na,ex(1)} \cdot f(\lambda)_{m,ex,460} + a_{Na,em(1)} \cdot f(\lambda)_{m,em,556} + a_{Na,p} \cdot f(\lambda)_{m,ex,452} \cdot f(\lambda)_{m,em,544} \quad \text{EQ 11:}$$

$$s_{K,m} = a_{K,0} + a_{K,ex(1)} \cdot f(\lambda)_{m,ex,458} + a_{K,em(1)} \cdot f(\lambda)_{m,em,556} + a_{K,p} \cdot f(\lambda)_{m,ex,452} \cdot f(\lambda)_{m,em,544} \quad \text{EQ 12:}$$

$$s_{Cl,m} = a_{Cl,0} + a_{Cl,em} \cdot f(\lambda)_{m,em,536} + a_{Cl,ex,1} \cdot f(\lambda)_{m,ex,470} + a_{Cl,ex,2} \cdot f(\lambda)_{m,ex,470}^2 \quad \text{EQ 13:}$$

In the electrolyte-specific, module-specific normalization factor equations above, all $f(\lambda)_m$ values are fractional areas under the curves of the standardized or mathematically normalized excitation or emission sensitivity spectra for the particular module tested. For example, $f(\lambda)_{m,em,556}$ indicates the fractional area under the standardized or normalized module emission spectrum curve from 500 nm through 556 nm. Similarly, $f(\lambda)_{m,ex,470}$ indicates the fractional area under the standardized or normalized module excitation spectrum from 470 nm through 500 nm. Note that 500 nm is here always the starting or ending wavelength for module emission sensitivity or excitation spectra, respectively. However, depending on a particular purpose, the specific wavelength range (or ranges) used to calculate these areas may be varied.

For "EQ 11" through "EQ 13" above, exemplary wavelength function coefficients were determined by least-squares optimization of data from a large training set of analyzers. In tabular form, these coefficients are:

TABLE 1

| | Na and K coefficients | | | |
|---|---|---|---|---|
| | $a_0$ | $a_{ex(1)}$ | $a_{em(1)}$ | $a_p$ |
| for Na norm. factor | 0.668830 | 0.493135 | 0.946124 | −1.592978 |
| for K norm. factor | 0.318983 | 0.588290 | 1.695024 | −2.068804 |

TABLE 2

| | Cl coefficients | | | |
|---|---|---|---|---|
| | $a_0$ | $a_{em}$ | $a_{ex,1}$ | $a_{ex,2}$ |
| for Cl norm. factor | 0.935330 | −0.066119 | 0.425202 | −1.086057 |

In general, the function, functions, or combinations thereof that best fit the target normalization factors for a wide range of analyzers are selected. Alternatively, the selected function, functions, or combinations thereof may be used to assign a target normalization factor for a module whose target normalization factor is not known. In the first case, the normalization factor, $s_e$, is calculated in accordance with these functions of wavelength characteristics, $f(\lambda)_{e,ex}$ and $f(\lambda)_{e,em}$, to optimize the fit between the calculated and target normalization factor according to a function, as mentioned above, such as:

$$s_e = c_{e,em} \times f(\lambda)_{e,em} + c_{e,ex} \times f(\lambda)_{e,ex} + c_{e,0} \quad \text{EQ 14}$$

where $c_{e,em}$, $c_{e,ex}$, and $c_{e,0}$ are optimization parameters, where this equation is the same as "EQ 3," and where this is a simpler form than was shown in the example above. In the second case, the same functions of wavelength characteristics, $f(\lambda)_{e,ex}$ and $f(\lambda)_{e,em}$, each with values particular to the module being normalized, are applied to the predetermined normalization factor equation, using the predetermined optimization parameters, to assign a normalization factor for the module.

As such, for a given analyzer (or, more specifically, for the module thereof), a set of normalization factors, $s_e$, may be determined, with each normalization factor corresponding to a particular electrolyte sensor. Thus, after using the analyzer to run a particular slide containing a sample thereon, the normalization factor specific to the analyzer and the electrolyte sensor contained on the slide may then be used, in conjunction with the analyzer response to the electrolyte sensor and the slide's lot calibration, to correct, or normalize the output value of the analyzer into a concentration measurement of the electrolyte within the sample.

Embodiment 2

In another embodiment, as discussed above, the overlap between the spectra, e.g., the excitation and emission spectra, of the module and the slide, e.g., the fluorophore or sensor, is analyzed to determine the normalization factor for a particular analyzer and electrolyte to be detected. The relative overlap between the spectra is important because, for example, a particular module may more effectively excite the fluorescence of an "early" or "late" sensor (i.e., where there is greater overlap between the spectra) or may less effectively excite the "late" or "early" fluorescence of the sensor (i.e., where the spectra are less overlapped) thereby introducing a bias (or biases) toward and/or against a particular sensor's analyzer response. However, by analyzing the overlap between the spectra of the module and the "early" and "late" sensor spectra, such variations, or biases, can be accounted for in determining the normalization factor for a particular module and electrolyte (or the particular fluorophore used to detect that electrolyte).

First, the module excitation spectrum data, relative irradiance as a function of wavelength, $f(\lambda_i)_{m,ex}$, is collected as (wavelength, relative irradiance) ordered pairs and is indexed accordingly. Similarly, the slide excitation spectrum data, relative fluorescence as a function of excitation wavelength, $f(\lambda_i)_{e,early,ex}$ and $f(\lambda_i)_{e,late,ex}$, is collected as (wavelength, fluorescence intensity) ordered pairs in both early and late readings, respectively, as discussed above. However, in this embodiment, the data need not be standardized or mathematically normalized, although the data may be filtered. The ratio of the overlaps of module and "early" and "late" slide excitation spectra are calculated to obtain a function of excitation spectra overlap:

$$f(\lambda)_{m,e,l,c,ex,ovr} = \left( \frac{\sum_{i=1}^{N_{ex}} f(\lambda_i)_{m,ex} \times f(\lambda_i)_{e,l,c,late,ex}}{\sum_{i=1}^{N_{ex}} f(\lambda_i)_{m,ex} \times f(\lambda_i)_{e,l,c,early,ex}} \right) \quad \text{EQ 15}$$

In some embodiments, explicit consideration of slide lot/and sample concentration c may be dropped.

Similarly, the module emission spectrum data, irradiance sensitivity as a function of wavelength, $f(\lambda_i)_{m,em}$, is collected as (wavelength, relative irradiance sensitivity) ordered pairs and is indexed accordingly and the slide emission spectrum data, relative fluorescence as a function of emission wavelength, $f(\lambda_i)_{e,early,em}$ and $f(\lambda_i)_{e,late,em}$, is collected as (wavelength, fluorescence intensity) ordered pairs in both early and late readings, respectively, as discussed above. As with the excitation data, this data need not be standardized or mathematically normalized, but may be filtered. The ratio of the overlaps of module sensitivity and "early" and "late" slide emission spectra are calculated to obtain a function of emission spectra overlap:

$$f(\lambda)_{m,e,l,c,em,ovr} = \left( \frac{\sum_{i=1}^{N_{em}} f(\lambda_i)_{m,em} \times f(\lambda_i)_{e,l,c,late,em}}{\sum_{i=1}^{N_{em}} f(\lambda_i)_{m,em} \times f(\lambda_i)_{e,l,c,early,em}} \right) \quad \text{EQ 16}$$

where, again, explicit consideration of slide lot l and sample concentration c may be dropped in some embodiments.

Using the above data sets, "EQ 15" and "EQ 16," the ratios of the overlaps of module and sensor excitation and emission spectra can be used to fit a target normalization factor with an analytical form similar to "EQ 14," where, dropping the module, slide lot, and concentration indices, $f(\lambda)_{e,ex,ovr}$ (from "EQ 15") is substituted for $f(\lambda)_{e,ex}$ and $f(\lambda)_{e,em,ovr}$ (from "EQ 16") is substituted for $f(\lambda)_{e,em}$.

A simpler equation, the same as "EQ 4" but in different form, is also considered:

$$s_e = c_{e,1} \times f(\lambda)_{e,ex,ovr} \times f(\lambda)_{e,em,ovr} + c_{e,0} \quad \text{EQ 17:}$$

as are more complicated forms involving linear and non-linear combinations of the two spectrum overlap ratios and their product, or any other suitable equations incorporating the principles of the present disclosure.

As such, similarly to the previous embodiment, for a given module, a set of normalization factors, $s_e$, may be determined, with each normalization factor corresponding to a particular electrolyte sensor. Note again that the concentration subscript is dropped if normalization factors are averaged for multiple concentrations. Thus, after using the analyzer to run a particular sample, the normalization factor specific to the analyzer and the electrolyte sensor on the slide containing the sample may then be used, in conjunction with the slide's lot calibration, to correct or normalize the output value of the analyzer into a concentration measurement of the electrolyte within the sample.

As can be appreciated, once the set of normalization factors, $s_e$, for a given module have been determined, e.g., according to any of the embodiments above, the particular module need not be re-normalized by running a plurality of samples of known concentration thereon. Rather, the sample need only be run on the module to provide an analyzer response value, which, in conjunction with the slide's lot calibration (determined independently) and the normalization factor specific to that module and electrolyte to be detected, is used to determine the electrolyte concentration of the specific electrolyte within the sample.

From the foregoing and with reference to the various figure drawings, those skilled in the art will appreciate that certain modifications can also be made to the present disclosure without departing from the scope of the same. While several embodiments of the disclosure have been shown and described, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A method of normalizing an analyzer, the method comprising the steps of:
   measuring an excitation spectrum of the analyzer;
   determining at least one wavelength characteristic function of the excitation spectrum of the analyzer;
   measuring an emission sensitivity spectrum of the analyzer;
   determining at least one wavelength characteristic function of the emission sensitivity spectrum of the analyzer; and
   determining a normalization factor based at least upon the at least one wavelength characteristic function of the excitation spectrum and the at least one wavelength characteristic function of the emission sensitivity spectrum, wherein, the normalization factor is used to normalize an analyzer response value of the analyzer.

2. The method according to claim 1, wherein the excitation spectrum of the analyzer is measured to obtain a data set of relative irradiance as a function of wavelength of the excitation spectrum.

3. The method according to claim 1, wherein the emission sensitivity spectrum of the analyzer is measured to obtain a data set of relative irradiance sensitivity as a function of wavelength of the emission sensitivity spectrum.

4. The method according to claim 1, wherein, the at least one wavelength characteristic function of the excitation spectrum includes at least one of: a wavelength centroid function, a function representing an area under at least a portion of the excitation spectrum, a function representing a wavelength at which a relative irradiance exceeds a first predetermined value, a function representing a wavelength at which the relative irradiance falls below a second predetermined value, and a function representing a relative irradiance value at a particular wavelength.

5. The method according to claim 1, wherein, the at least one wavelength characteristic function of the emission sensitivity spectrum includes at least one of: a wavelength centroid function, a function representing an area under at least a portion of the emission sensitivity spectrum, a function representing a wavelength at which a relative irradiance sensitivity exceeds a first predetermined value, a function representing a wavelength at which the relative irradiance sensitivity falls below a second predetermined value, and a function representing a relative irradiance sensitivity at a particular wavelength.

6. The method according to claim 1, wherein, the normalization factor is determined in accordance with at least one of a plurality of wavelength characteristic functions of the excitation spectrum and at least one of a plurality of wavelength characteristic functions of the emission sensitivity spectrum, the at least one wavelength characteristic function of the excitation spectrum and the at least one wavelength characteristic function of the emission sensitivity spectrum selected by comparison to a target normalization factor.

7. The method according to claim 1, wherein the excitation spectrum is measured using a spectrometer and wherein the emission sensitivity spectrum is measured using a monochromator.

8. The method according to claim 1, wherein a set of normalization factors is determined, each normalization factor corresponding to a different sensor to be detected by the analyzer.

9. The method according to claim 8, wherein the normalization factor for each sensor is determined in accordance with at least one fitting parameter specific to the sensor.

10. A method of normalizing an analyzer in accordance with a specific sensor to be detected by the analyzer, the method comprising the steps of:

measuring an excitation spectrum of the analyzer;
measuring an excitation spectrum of the sensor;
determining a first parameter based at least upon the overlap of the excitation spectrum of the analyzer and the excitation spectrum of the sensor;
measuring an emission sensitivity spectrum of the analyzer;
measuring an emission spectrum of the sensor;
determining a second parameter based at least upon an overlap of the emission sensitivity spectrum of the analyzer and the emission spectrum of the sensor; and
determining a normalization factor based at least upon at least one of the first and second parameters, wherein, the normalization factor is used to normalize an analyzer response value of the analyzer and the sensor.

11. The method according to claim 10, wherein the step of measuring the excitation spectrum of the sensor includes:
measuring an early excitation spectrum of sensor;
measuring a late excitation spectrum of the sensor; and
wherein, the first parameter is a ratio of the overlap of the excitation spectrum of the analyzer with the late excitation spectrum of the sensor divided by the overlap of the excitation spectrum of the analyzer with the early excitation spectrum of the sensor.

12. The method according to claim 10, wherein the step of measuring the emission spectrum of the sensor includes:
measuring an early emission spectrum of sensor;
measuring a late emission spectrum of the sensor; and
wherein, the second parameter is a ratio of the overlap of the emission sensitivity spectrum of the analyzer with the late emission spectrum of the sensor divided by the overlap of the emission sensitivity spectrum of the analyzer with the early emission spectrum of the sensor.

13. The method according to claim 10, wherein at least one of the excitation spectrum of the analyzer and the emission sensitivity spectrum of the analyzer is measured to obtain a data set of relative irradiance as a function of wavelength of the excitation spectrum of the analyzer and the emission sensitivity spectrum of the analyzer, respectively.

14. The method according to claim 10, wherein at least one of the excitation spectrum of the sensor and the emission spectrum of the sensor is measured to obtain a data set of relative fluorescence as a function of wavelength of the excitation spectrum of the sensor and the emission spectrum of the sensor, respectively.

15. The method according to claim 10, wherein the normalization factor is determined in accordance with at least one fitting parameter specific to the sensor.

16. The method according to claim 10, wherein the normalization factor is determined in accordance with a target normalization factor.

* * * * *

UNITED STATES PATENT AND TRADEMARK OFFICE
CERTIFICATE OF CORRECTION

| | | |
|---|---|---|
| PATENT NO. | : 8,760,645 B2 | Page 1 of 1 |
| APPLICATION NO. | : 13/114261 | |
| DATED | : June 24, 2014 | |
| INVENTOR(S) | : Garland Christian Misener, James Edward Milan and Robert W. Lachapelle | |

It is certified that error appears in the above-identified patent and that said Letters Patent is hereby corrected as shown below:

On the Title Page
At Item (73), Assignee, please change "IDEXX Laboratories Inc., Westbrook, MA (US)" to --IDEXX Laboratories Inc., Westbrook, ME (US)--

Signed and Sealed this
Ninth Day of September, 2014

Michelle K. Lee
*Deputy Director of the United States Patent and Trademark Office*